United States Patent [19]
Nikles

[11] 4,012,435
[45] Mar. 15, 1977

[54] CARBAMATES
[75] Inventor: Erwin Nikles, Liestal, Switzerland
[73] Assignee: Ciba-Geigy AG, Basel, Switzerland
[22] Filed: Sept. 24, 1968
[21] Appl. No.: 762,144
[30] Foreign Application Priority Data
Sept. 25, 1967 Switzerland .............. 13375/67
[52] U.S. Cl. .............. 260/479 C; 260/348 C; 424/300
[51] Int. Cl.² ................. C07C 125/06

[58] Field of Search .............. 260/479 C

Primary Examiner—Anton H. Sutto
Attorney, Agent, or Firm—Frederick H. Rabin; Harry Goldsmith; Joseph G. Kolodny

[57] ABSTRACT

The invention comprises [5,8-dihydro-5,8-endomethylene-1-naphthyl]-carbamates and their use in pesticides.

6 Claims, No Drawings

CARBAMATES

The present invention provides compounds of the formula

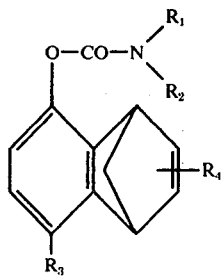

(I)

in which
- $R_1$ represents a hydrogen atom or a lower alkyl group,
- $R_2$ represents a hydrogen atom, the methyl or an acyl group,
- $R_3$ represents a hydrogen atom, a lower alkoxy group or a carbamoyloxy group substituted by lower alkyl groups,
- $R_4$ represents a hydrogen atom or a methyl group, and in which the double bond in the 6,7-position may be epoxidized or hydrogenated.

The present invention also provides a pesticidal preparation, which comprises a compound of the formula (I) wherein $R_1$, $R_2$, $R_3$ and $R_4$ have the meanings given above, together with a suitable carrier.

These preparations may further contain one or more than one of the following additives: a solvent, a diluent, a dispersant, a wetting agent, an emulsifier, a thickener and further known pesticids.

The new carbamates may be prepared by the methods conventionally used for the manufacture of this type of compound, for example, by reaction of suitable endomethylenenaphthols with alkylisocyanates or with carbamoylchlorides which may be substituted as shown for $R_1$ and $R_2$ above, or by reaction of suitable endomethylene-naphtholo-chlorocarbonates with methylamine or an amine substituted as shown above for $R_1$ and $R_2$.

The endomethylene dihydronaphthols and tetrahydronaphthols required for the manufacture of the carbamates according to this invention are either known or are accessible by known methods. For example, 5,8-dihydro-5,8-endomethylene-1,4-naphthohydroquinone is obtained by rearrangement in the presence of an acid or basic catalyst, for example, hydrogen bromide or triethylamine, of the Diels-Alder adduct of 1 mol each of cyclopentadiene and benzoquinone; on alkylation this leads to the 4-alkoxy-5,8-dihydro-5,8-endomethylene-1-naphthols.

The conversion of 5,8-dihydro-5,8-endomethylene-1,4-naphthohydroquinone into 5,8-endomethylene-5,6,7,8-tetrahydro-1-naphthol, accompanied by elimination of a hydroxyl group, proceeds relatively smoothly when, in a first stage, the starting compound is reacted with an equimolecular proportion of 1-phenyl-5-chlorotetrazole in the presence of potassium carbonate, and the resulting mono-phenyltetrazolyl ether is then subjected to hydrogenating scission with palladium carbon (J. Am. Chem. Soc. 88, page 4271 [1966]).

The invention includes also the new carbamates of the general formula

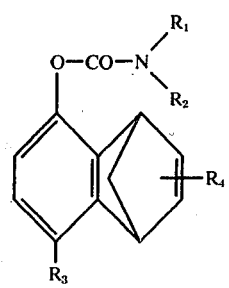

(I)

in which $R_1$ represents a hydrogen atom or a lower alkyl group, $R_2$ represents a hydrogen atom, the methyl or an acyl group, $R_3$ represents a hydrogen atom, a lower alkoxy group or a group substituted by lower alkyl groups, $R_4$ represents a hydrogen atom or a methyl group, and in which the double bond in the 6,7-position may be expoxidized or hydrogenated.

Especially important are the carbamates of the formula:

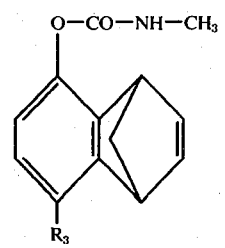

(II)

in which $R_3$ represents a hydrogen atom, the methoxy group or a carbamoyloxy group substituted by one or two lower alkyl groups, and the isolated double bond in the 6,7-position may be hydrogenated or epoxidized.

The carbamates of this invention surprisingly display a wide spectrum of biocidal properties which are advantageous in comparison with those of known carbamates.

As herbicides, they may be used against mono- and dicotyledons both in the pre-emergence and postemergence method, and when used in appropriate doses for this purpose, they are readily compatible with certain culture plants.

In this connection, it has been observed, with surprise, that when the concentration is lowered beyond the phytotoxicity level in any given case, the compounds are still very effective against insects, infestation by fungi and also against certain species of nematodes. This effect is observed at all stages of development of the pests named.

The carbamates of the invention are specially efficacious in the total destruction of pests of the Akarina order. In comparison with this effect, their toxicity towards warm-blooded beings is low.

It should also be mentioned that very favourable results have been achieved in combating bacteria.

The combating of molluscs, especially of Gastropodes, with the new carbamates has shown very good results, and an advantageously low toxicity towards fish has been found.

In the first place, however, the above-mentioned carbamates are distinguished by their insecticidal activity in addition to their acaricidal activity. Especially valuable are the compounds of the formulae

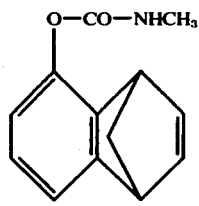
(2)

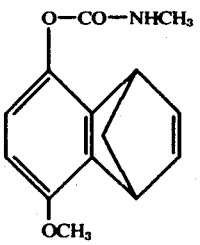
(4)

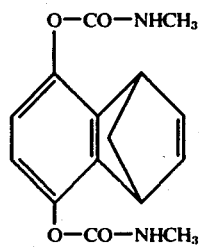
(8)

as well as the 6,7-dihydro compounds Nos. 15, 17 and 22 (see following Table) derived from them.

For example, the carbamates of the general formula I display a very strong activity against houseflies, midges, bedbugs, aphids, caterpillars, cockroaches and beetles, for example, cornweevils and colorado beetles, as well as against mites and ticks. Their contact activity is superior to that of the known active substance "Carbaryl" (=N-methyl-α-naphthylcarbamate).

Accordingly, the new carbamates are extremely suitable for combating harmful insects in all their stages of development, including soil insects and acarides.

Solutions of the compound of the general formula (I) for direct spraying may be prepared, for example, by using petroleum fractions of a high to medium boiling range, for example, Diesel oil or kerosene, coal tar oil and oils of vegetable or animal origin, or with hydrocarbons, for example, alkylated naphthalenes, or tetrahydronaphthalene, if desired with the use of xylene mixtures, cyclohexanols or ketones, or chlorinated hydrocarbons for example, trichloroethane, tetrachloroethane, trichloroethylene or tri- or tetrachlorobenzenes. It is advantageous to use organic solvents that boil above 100° C.

It is especially advantageous to prepare aqueous forms of application from emulsion concentrates, pastes or wettable spray powders by the addition of water thereto. Suitable emulsifiers or dispersants are nonionic products, for example, condensation products of aliphatic alcohols, amines or carboxylic acids with a long-chain hydrocarbon residue containing from about 10 to 20 carbon atoms with ethylene oxide, for example, the condensation product of octadecyl alcohol with 25 to 30 mols of ethylene oxide, or of commercial oleylamine with 15 mols of ethylene oxide, or of dodecylmercaptan with 12 mols of ethylene oxide. As anionic amulsifiers that may be used there may be mentioned: the sodium salt of dodecyl alcohol sulphuric acid ester, the sodium salt of dodecylbenzenesulphonic acid, the potassium or triethanolamine salt of oleic acid or of abietic acid or of a mixture of these two acids, or the sodium salt of a petroleum-sulphonic acid. Suitable cationic dispersants are: quaternary ammonium compounds, for example, cetyl pyridinium bromide or dihydroxyethyl benzyldodecyl ammonium chloride.

In the manufacture of dusting and casting preparations there may be used as solid vehicles: talcum, kaolin, bentonite, calcium carbonate, calcium phosphate, or coal, cork meal, wood meal or other materials of vegetable origin. It is also very advantageous to use the preparations in granular form. The various forms of application may contain the usual additives for improving the distribution, the adhesion, the stability towards rain or the penetration, for example, acids, resins, glue, casein or alginates.

The preparations of this invention may be used by themselves or in conjunction with conventional pesticides, especially insecticides, acaricides, nematocides, bactericides and/or fungicides in plant cultivation or in conjunction with fertilisers.

The following Examples illustrate the invention, the parts being by weight.

EXAMPLE 1 a.
5,8-Dihydro-5,8-endomethylene-4-methoxynaphthol-(1)

77 Parts of dimethylsulphate are added in portion, while stirring at a temperature of from 20° to 25° C, to a solution of 85 parts of 5,8-dihydro-5,8-endomethylene-1,4-naphthohydroquinone in 500 parts by volume of 4N-sodium hydroxide solution (prepared under nitrogen). The whole is stirred for 3 hours at room temperature, and the dimethylether formed is filtered off. The filtrate is neutralised with hydrochloric acid and extracted with toluene and the extract evaporated, to leave 5,8-dihydro-5,8-endomethylene-4-methoxynaphthol-(1) as a viscid oil.

b.
[5,8-Dihydro-5,8-endomethylene-4-methoxy-1-naphthyl]-N-methyl carbamate (Compound 4)

20 Parts of methyl isocyanate are added drop by drop at 30° to 35° C to a solution of 51 parts of 5,8-dihydro-5,8-endomethylene-4-methoxynaphthol-(1) and 0.2 part of triethylenediamine in 200 parts by volume of carbon tetrachloride. The solution is maintained for 14 hours at 35° C, and then for 2 days at −8° C. The precipitate formed is crystallised at −8° C from methanol and acetone; it melts at 114° − 115° C.

c. When the product (b) is hydrogenated in methanol with palladium carbon as catalyst, it yields (5,8-endomethylene-4-methoxy-5,6,7,8-tetrahydro-1-naphthyl)-N-methyl-carbamate (compound 17).

d. When compound 17 is boiled for 2 hours with acetic anhydride in the presence of a catalytic amount of concentrated sulphuric acid, it yields the oily (5,8-endomethylene-4-methoxy-5,6,7,8-tetrahydro-1-naphthyl)-N-acetyl-N-methyl-carbamate (compound 19).

EXAMPLE 2

5,8-Dihydro-5,8-endomethylene-1,4-naphthylene-bis-(N-methyl-carbamate (Compound 8)

340 Parts of 5,8-dihydro-5,8-endomethylene-1,4-naphthohydroquinone and 1 part of diethylenetriamine are dissolved in 1500 parts by volume of dry ether and 245 parts of methyl isocyanate are added in portions. After the exothermic reaction has subsided, the batch is heated for 20 hours at 35° C. The product which has crystallized out is filtered off and recrystallized at −8° C from ethyl acetate; it melts at 149° to 151° C.

The following compounds of the formula III may be prepared in one of the ways described above:

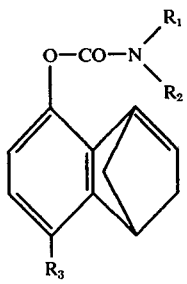

| Compound No. | 6.7-position | $R_1$ | $R_2$ | $R_3$ |
|---|---|---|---|---|
| 1 | — | $CH_3$ | $-CH_3$ | H |
| 2 | — | $CH_3$ | H | H |
| 3 | — | $CH_3$ | $-CO-CH_3$ | H |
| 4 | — | $CH_3$ | H | $-OCH_3$ |
| 5 | — | $CH_3$ | H | $-OC_2H_5$ |
| 6 | — | $CH_3$ | $-CH_3$ | $-OCH_3$ |
| 7 | — | H | H | $-OCH_3$ |
| 8 | — | $CH_3$ | H | $-O-CO-NH-CH_3$ |
| 9 | — | H | H | $-O-CO-NH_2$ |
| 10 | — | $CH_3$ | $-CH_3$ | $-O-CO-N(CH_3)_2$ |
| 11 | — | $CH_3$ | $-CO-CH_3$ | $-O-CO-N\begin{matrix}CH_3\\COCH_3\end{matrix}$ |
| 12 | — | $CH_3$ | $-CO-CH_3$ | $-OCH_3$ |
| 13 | — | $CH_3$ | $CH_3$ | $-OC_2H_5$ |
| 14 | — | $C_2H_5$ | H | $-O-CO-NHC_2H_5$ |
| 15 | 6.7 dihydro | $CH_3$ | H | H |
| 16 | 6.7 dihydro | $CH_3$ | $CH_3$ | H |
| 17 | 6.7 dihydro | $CH_3$ | H | $-OCH_3$ |
| 18 | 6.7 epoxy | $CH_3$ | H | $-O-CO-NHCH_3$ |
| 19 | 6.7-dihydro | $CH_3$ | $-COCH_3$ | $-OCH_3$ |
| 20 | 6.7-epoxy | $CH_3$ | H | $-OCH_3$ |
| 21 | 6.7-dihydro | $CH_3$ | $CH_3$ | $-O-CO-N(CH_3)_2$ |
| 22 | 6.7-dihydro | $CH_3$ | H | $-O-CO-NHCH_3$ |

It is also possible to manufacture derivatives in which a methyl group occupies one of the 5-positions in the cyclopentene portion of the formula:

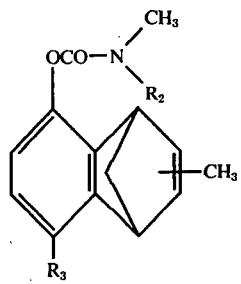

in which $R_2$ and $R_3$ have the same meanings as in formula I.

EXAMPLE 3

Dusting Agents

Equal parts of one of the active substances of the formula (I) and of precipitated silicic acid are mixed and finely ground. By incorporation of kaolin or talcum, dusting agents having the desired concentration of active substance may be prepared therefrom. In general, preparations containing 1 to 6 % of active ingredient are preferred.

Spray Powder

To manufacture a spray powder, the following ingredients, for example, are mixed and finely ground:
 50 parts of active substance (one of the compounds of the formula (I))
 20 parts of Hisil (highly adsorptive precipitated silicic acid)
 25 parts of bolus (kaolin)
 3.5 parts of an adduct of p-tertiary octylphenol with ethylene oxide
 1.5 parts of sodium 1-benzyl-2-stearylbenzimidazole-6,3'-disulphonate.

Emulsion Concentrate

Readily soluble active substances may also be formulated in the form of emulsion concentrates in the following manner:

20 Parts of active substance, 70 parts of xylene and 10 parts of a mixture of an adduct of an alkylphenol with ethylene oxide and calcium dodecylbenzenesulphonate. On dilution with water to the desired concentration, a sprayable emulsion is obtained.

EXAMPLE 4

Compound 4 was formulated with talcum as described in Example 3 and used as dusting preparation against various pests. After 2 hours' exposure, a 100 % destructive effect was recorded against the under-mentioned pests, with the quantity of active substance shown:

| Pest tested | mg of active substance per sq.m |
|---|---|
| German cockroach (Phyllodromia germanica) | 50 |
| American cockroach (Periplaneta americana) | 12 |
| Russian cockroach (Blatta orientalis) | 50 |
| larder beetle larvae (Dermestes frischii) | 50 |

| Pest tested | mg of active substance per sq.m |
|---|---|
| domestic cricket (Acheta domestica) | 50 |

EXAMPLE 5

Activity against midges

A. Female midges are kept for 6 hours on a layer prepared from an acetonic solution of the active substance in Petri dishes of 11 cm diameter. The layer is prepared by pouring 1 ml of a dilute solution of the active substance into the dish, and then allowing the acetone to evaporate so that a concentration of 1.0, 0.1, 0.01 and 0.001 mg per dish is obtained.

The midges are first cooled in ice and then 10 females are counted into each dish. At each concentration, 4 tests are made.

When a concentration of only 0.001 mg per dish was used, compound 4 revealed the following mortality in percent after the indicated, independently measured time intervals:

| Pest tested | after 45 | 90 | 180 | 360 mins. |
|---|---|---|---|---|
| Aedes aegypti | 65% | 100% | | |
| Anopheles stephensi | 15% | 40% | 95% | 100% |

B. Larvae test: Dilution series starting at 1 part per million were prepared from an emulsion of the active substance in tap water at room temperature, and these dilutes were tested against midge larvae in the $L_1$-stage. The evaluation was made after 24 hours.

Compound 4, used in a concentration of 0.4 part per million, produced a 100 % destructive effect.

EXAMPLE 6

Activity against ticks and chicken mites

A number of the organisms tested are immersed for 1 minute in a small glass tube containing each 2 ml of the emulsified active substance in different aqueous concentrations; the tube is then closed with a standard cottonwool stopper and turned upside down. After the solution of the active substance has been absorbed, the test organisms are kept for 14 and 3 days respectively, after which evaluation is carried out.

Compound 4 revealed a 100 % lethal effect on the undermentioned test organisms at the indicated concentrations:

| Number of organisms tested | Organism tested | tested for days | concentration ppm | No. of tests |
|---|---|---|---|---|
| 10 | Rhipicephalus bursa (adult, hungry) | 14 | 100 | 3 |
| 5 | Amblyomma variegatum (hungry) | 14 | 100 | 3 |
| 10-20 | Boophilus microplus | 3 | 10 | 3 |
| 10-20 | Dermanyssus gallinae | 3 | 1 | 3 |

Similar, favourable results were obtained with compounds Nos. 8, 9, 11, 15 and 21.

EXAMPLE 7

Activity against larvae of Lucilia sericata (blow fly)

Freshly hatched maggots are exposed to a mixture of 2 g of chopped horse flesh and an aqueous series of dilutions of the active substance 4 with concentrations of 48, 24, 12, 6, 3, 1.5 and 0.75 parts per million. On different days, 3 parallel tests with different fly generations and new dilution series are carried out.

The limit concentration for a 100 % lethal effect, measured after 24 hours, was found to be 3 ppm of active substance.

Similar results were obtained with compounds Nos. 8, 10, 11, 15 and 16.

EXAMPLE 8

Activity against bedbugs

As in Example 5(A), Petri dishes with filter paper impregnated with active substance were prepared. 1 Hour after having impregnated the filter papers, 10 test organisms of Cimex lectularius are introduced into the dishes. Evaluation is carried out after 45, 90, 180 and 360 minutes, and after 24 and 48 hours. Three parallel tests are carried out.

At a concentration of 1 mg per dish (= 1 g per 6 sq.m) compound 4 revealed the following lethal speeds:

| after 45 | 90 | 180 minutes |
|---|---|---|
| 15% | 85% | 100% mortality. |

The activities of compounds 5, 8, 9 and 10 are of the same order of magnitude.

I claim:

1. A carbamate of the general formula

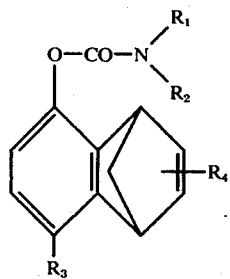

in which $R_1$ represents a hydrogen atom or a lower alkyl group, $R_2$ represents a hydrogen atom, the methyl or acetyl group, $R_3$ represents a hydrogen atom, a lower alkoxy group or a carbamoyloxy group substituted by lower alkyl groups, $R_4$ represents a hydrogen atom or a methyl group, and in which the double bond in the 6,7-position may be hydrogenated.

2. A carbamate as claimed in claim 1 of the formula

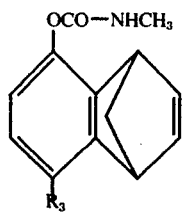

in which $R_3$ represents a hydrogen atom, the methoxy group or a carbamoyloxy group substituted by one or two lower alkyl groups, and in which the isolated 6,7-double bond may be hydrogenated.

3. The carbamate as claimed in claim 1 of the formula

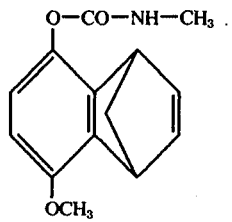

4. The carbamate as claimed in claim 1 of the formula

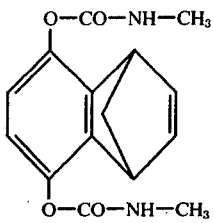

5. A compound of the formula

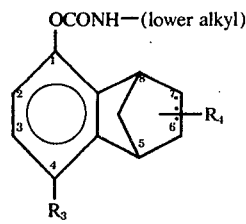

wherein $R_3$ represents hydrogen or lower alkoxy and $R_4$ represents H or methyl, in which the symbol ⋯ represents a single or double bond and wherein $R_4$ is attached at either the 6- or 7-position.

6. A compound of the formula

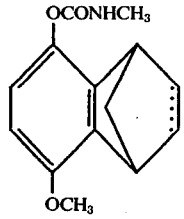

in which the symbol ⋯⋯ represents a single or double bond.

* * * * *